United States Patent [19]

Collier et al.

[11] Patent Number: 5,130,254
[45] Date of Patent: Jul. 14, 1992

[54] METHOD FOR PIPETTING LIQUID FROM A SEALED CONTAINER

[75] Inventors: Charles F. Collier; James L. Seago, both of Wilmington, Del.; William G. DiMaio, Brookhaven, Pa.

[73] Assignee: E. I. Du Pont de Nemours and Company, Wilmington, Del.

[21] Appl. No.: 528,357

[22] Filed: May 25, 1990

[51] Int. Cl.⁵ .................. G01N 1/10; B01L 3/02
[52] U.S. Cl. ........................ 436/54; 436/180; 422/63; 422/100; 73/863.01
[58] Field of Search .............. 422/63, 67, 100; 436/180, 54; 73/863.01, 864.24, 864.25; 604/411, 415

[56] References Cited

U.S. PATENT DOCUMENTS

| | | | |
|---|---|---|---|
| 1,392,454 | 10/1921 | Seelman | 604/415 |
| 3,872,730 | 3/1975 | Ringrose et al. | 73/421 |
| 4,020,837 | 5/1977 | Larson | 604/411 |
| 4,244,478 | 1/1981 | Handman | 215/249 |
| 4,274,453 | 6/1981 | Lee | 604/411 |
| 4,545,497 | 10/1985 | Martha, Jr. | 215/253 |
| 4,655,763 | 4/1987 | Malcolm et al. | 604/411 |
| 4,673,404 | 6/1987 | Gustavsson | 604/411 |
| 4,756,201 | 6/1988 | Uffenheimer | 428/36.7 |
| 4,808,381 | 2/1989 | McGregor et al. | 422/100 |
| 4,815,325 | 3/1989 | Averette | 73/864 |
| 4,935,274 | 6/1990 | DeBenedictis et al. | 428/36.7 |

FOREIGN PATENT DOCUMENTS 0184359  8/1987  Japan .

*Primary Examiner*—Jill A. Johnston
*Assistant Examiner*—Jan M. Ludlow

[57] ABSTRACT

A probe is introduced through the elastomeric cap of a closed sample container and moved sideways to stretch the cap and thereby provide an air passage to atmosphere while the sample is aspirated.

7 Claims, 2 Drawing Sheets

METHOD FOR PIPETTING LIQUID FROM A SEALED CONTAINER

FIELD OF THE INVENTION

This invention relates to a method and apparatus for pipetting liquids from a sealed container and, more particularly, to a method and apparatus for reducing pressure differences between the interior and exterior of a sealed container, thereby permitting more accurate pipetting of liquids.

BACKGROUND OF THE INVENTION

It is desirable in automated chemical analyzers to store reagents in a resealable container. Such a container allows access by perforating the container's lid for removing fluid, and after fluid withdrawal automatically reseals the perforation in the container's lid. This resealing action, known as self healing is essential to controlling reagent integrity over time. There are many known containers of this type. One such container is sold for use with the Dimension ® Clinical Chemistry System by E. I. du Pont de Nemours and Co., Wilmington, DE 19898. Another such container and lid construction is described in a patent application entitled "Lid Structure" Ser. No. 07/237,011, filed Aug. 16, 1988 by DeBenedictis now U.S. Pat. No. 4,935,274.

Simultaneously however, the resealable lid/container structure which lengthens reagent life, also inhibits the ability of an automated chemical analyzer to accurately remove fluid from the container. This happens because the flexible or elastomeric material used for the lid seals tightly around the pipetting probe or needle when the probe is inside the container. When fluid is removed, a vacuum is produced because the seal does not allow air to enter. This vacuum could adversely affect pipetting performance.

This vacuum condition lasts over a period of time, depending on many variables, but has been observed to last for days. So the effect is felt on the immediate aspiration as well as those that which may be performed in the future. The effect of repeated aspirations from the same container can also be additive. Thus each time fluid is removed, the vacuum become greater and greater.

Accuracy is consistently affected the same way. When the reagent pump attempts to draw 100% of the quantity desired, what is actually withdrawn from the container is less than 100%, usually in the 90 to 95% range of that desired. This is what one would expect; the reagent pump is applying a vacuum to draw fluid in while the vacuum in the container is tending to pull the fluid out. The pump actually gets less than that desired.

Precision of the reagent delivery is also affected by the vacuum. More spread or greater imprecision is observed with the container vacuum. This imprecision is attributed to, among other, gas in the fluid line, varied vacuum levels producing different effects, and bouncing of the fluid miniscus when withdrawing the probe from the container. Such variables are difficult if not impossible to control, so a means of eliminating the vacuum is needed.

This is a recognized problem and various techniques have been employed in the prior art for reducing the effects of this vacuum phenomena that's created within sealed containers. Thus, Gustavsson in U.S. Pat. No. 4,673,404 discloses an adapter device for venting and pressure balancing a sealed vessel. A vent needle pierces the closure of the sealed vessel allowing the vessel to vent through a filter. An aspiration needle may enter the vessel through the sealing member and the vessel closure to aspirate fluid from the vessel. While this approach aids in solving the problem, it also creates unnecessary punctures in the cap which can cause loss of fluid from the vessel in the container due to evaporation.

Another approach was taken by Averette in U.S. Pat. No. 4,815,325. As may be seen in FIG. 4A, Averette uses a coaxial probe to aspirate fluid from a sealed vessel. After the probe penetrates the sealing member of the vessel, fluid from the vessel may be aspirated through the inner tube of the coaxial probe to the aspiration tubing. During aspiration, air is vented into the vessel through the vent tubing and down through the outer annulus of the probe to the opening in the side of the coaxial probe. While this is a satisfactory alternative, where cross contamination is a concern the carry-over problems can be severe.

Ringrose et al. in U.S. Pat. No. 3,872,730 discloses a device for sampling from a closed blood tube such as a "Vacutainer" tube. A dual needle probe penetrates the closure of the tube, allowing the first needle to vent the interior of the tube to atmosphere and the second needle to aspirate fluid from the tube. Here again, the double penetration which occurs each time a sample is taken leads to the more rapid deterioration of the integrity of the seal of the container.

Finally, Uffenheimer U.S. Pat. No. 4,756,201 discloses a device for sampling from a closed blood tube such as a "Vacutainer" tube. Referring to FIG. 1 of Uffenheimer, when the probe first enters the tube, through the closure, the shear valve is positioned such that ambient air in the equilibration chamber is allowed to vent into the tube. After venting the shear valve is repositioned to allow the pump to aspirate from the tube.

This arrangement, which requires air in the system from the valve down to the probe, to eliminate contaminating the container with fluid is not always a desirable solution to the problem.

BRIEF DESCRIPTION OF THE INVENTION

Many of the disadvantages of the prior art techniques for withdrawing samples from sealed containers are significantly reduced using the method and apparatus of this invention. Firstly, this invention is a method for withdrawing liquid samples from a sealed sample container having an axis, the container having an elastomeric closure lying along the axis, using a robotic aspirating probe, the probe affording degrees of linear motion along the axis and orthogonal to the axis, comprising the steps of: (a) introducing the probe through the closure into the container, (b) moving the probe orthogonally of the axis to stretch the closure, thereby opening a passageway adjacent the probe to atmosphere, (c) applying vacuum to the probe, thereby to aspirate a sample or reagent from the container, and (d) withdrawing the probe from the container and allowing the puncture area to reseal (heal) preventing reagent degradation.

In a preferred embodiment of the method of this invention, the probe is returned orthogonally to its axial position prior to performing step (b), i.e., before it is withdrawn from the container. Using the method of this invention, significantly increases the accuracy with which liquids may be pipetted liquids. This is done quite simply by reducing the pressure difference between the inside and outside of the sealed containers, by the simple approach of moving the probe laterally of the axis of the container. No additional mechanical features such as needles, etc. of the invention are necessary. Furthermore, the wiping action provided by the lid of the container removes any droplets which might otherwise contribute to pipetting imprecision.

Further according to the invention an apparatus for withdrawing liquid samples from a sealed sample container having an axis, the container having an elastomeric closure lying along the axis, using a robotic aspirating probe, the probe providing linear motion along the axis of the container and orthogonal to the axis, and means to control the robotic probe, is improved by means coupled to the control mean to initially introduce the probe through the closure into the container, means coupled to the control mean to move the probe orthogonally to the axis to stretch the closure, thereby opening a passageway adjacent the probe to atmosphere, means coupled to the control mean for applying vacuum to the probe, thereby to aspirate a sample from the container, and means coupled to the control mean for withdrawing the probe from the container. The apparatus is further improved by means for returning the probe orthogonally to its original position prior to the orthogonal movement. The probe desirably is provided with an outer sleeve to support its sideway movement when stretching the lid.

BRIEF DESCRIPTION OF THE DRAWINGS

The invention may be more easily understood by reference to the following description of the invention in conjunction with the accompanying drawings wherein.

DETAILED DESCRIPTION OF THE PREFERRED EMBODIMENT

Figure 1:
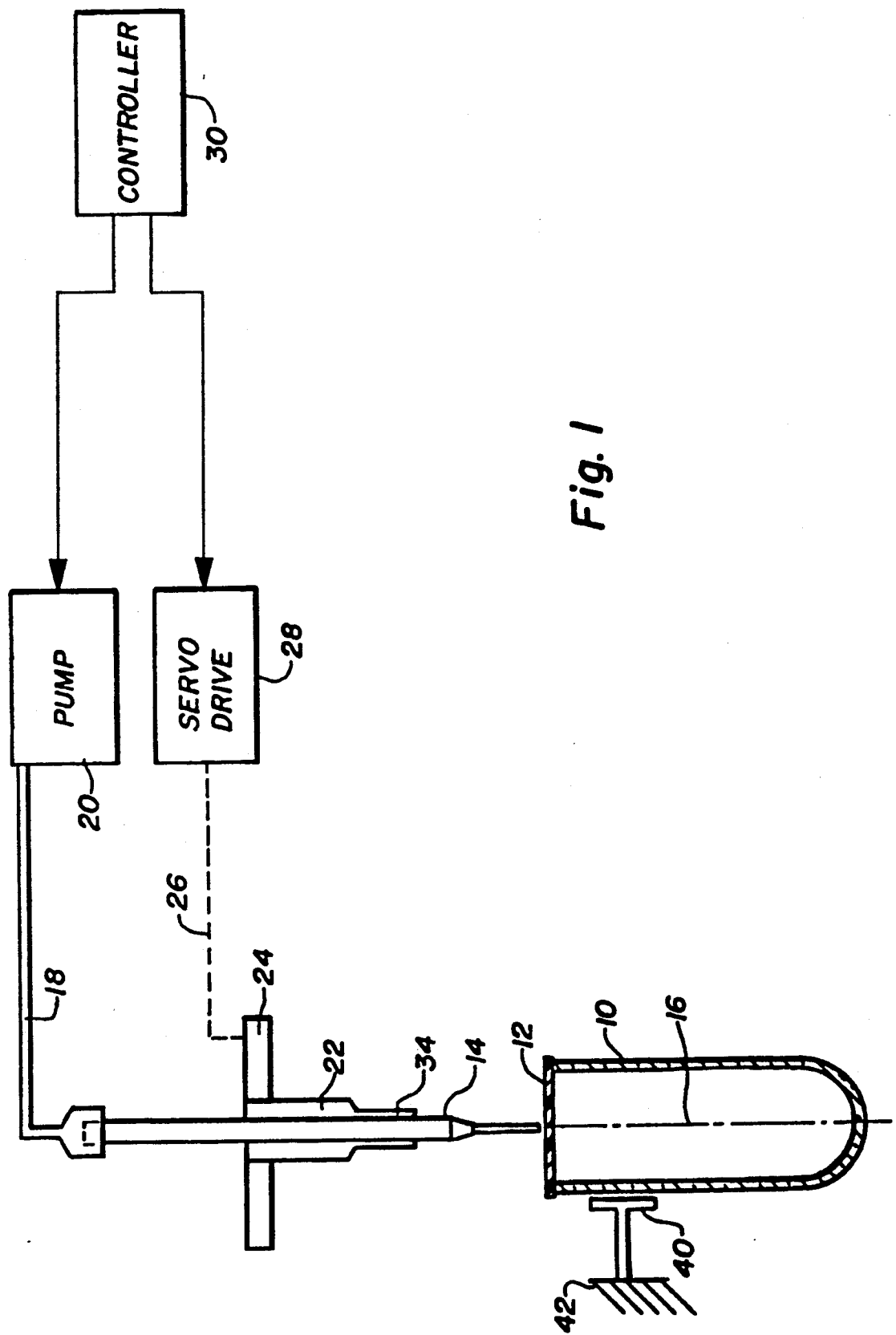
FIG. 1 is a diagrammatic view, partially in cross section, partially in block, depicting a pipette constructed in accordance with this invention.

There may be seen in FIG. 1 apparatus constructed in accordance with this invention which serves to reduce any vacuum or pressure present in a sealed sample container 10 so that liquids may be pipetted from the container with a high degree of accuracy. The container 10 is conventional may be constructed of any suitable material which is typically used for such purposes. Such containers are available on the open market and need only the chemically inert. The container 10 has a seal or closure lid 12 at the top thereof which again may be any suitable material. Although not at all critical, it is preferred that the containers used have a closure of the type sold with Du Pont's Dimension ® Clinical Chemistry System (E. I. du Pont de Nemours and Company). Such containers have an elastomeric closure 12 which comprises an elastomeric layer of suitable material, such as silicon rubber, covering a three ply laminate of a polyester film, a polyvinylidene chloride layer, and a polypropylene sheet. The laminate reduced evaporation and the elastomeric layer is self healing and effects a "squeegee" action to wipe the probe. A similar laminate is described in the DeBenedictis application. The particular lid structure used is not important so long as it is elastomeric, as will be described.

A probe 14 adapted to penetrate the lid 12 of the container 10 along the container axis 16 is attached through a tubing 18 to a vacuum pump 20. The probe 14 is hollow and is supported coaxially by a sleeve 22 secured thereabout and mounted in a holder 24. The sleeve and probe may be formed of any suitable material such as stainless steel. The holder 24 in turn 24 is adapted to be moved in an XZ sense (horizontal and vertical) through a linkage 26 by a servo drive 28 which is controlled by a controller 30. In similar manner the pump 20 is also controlled by the controller 30. The controller 30 may be any of the conventional controllers using microprocesser chips or otherwise. Any suitable robotic controller that may be used for this invention. Preferably, the controller may be that sold by E. I. du Pont de Nemours and Company for use on their Dimension ® System. Any other controllers are suitable for this purpose provided only that they have the ability to provide lateral and vertical movement of the probe with approximately three to four pounds force.

Figure 2:
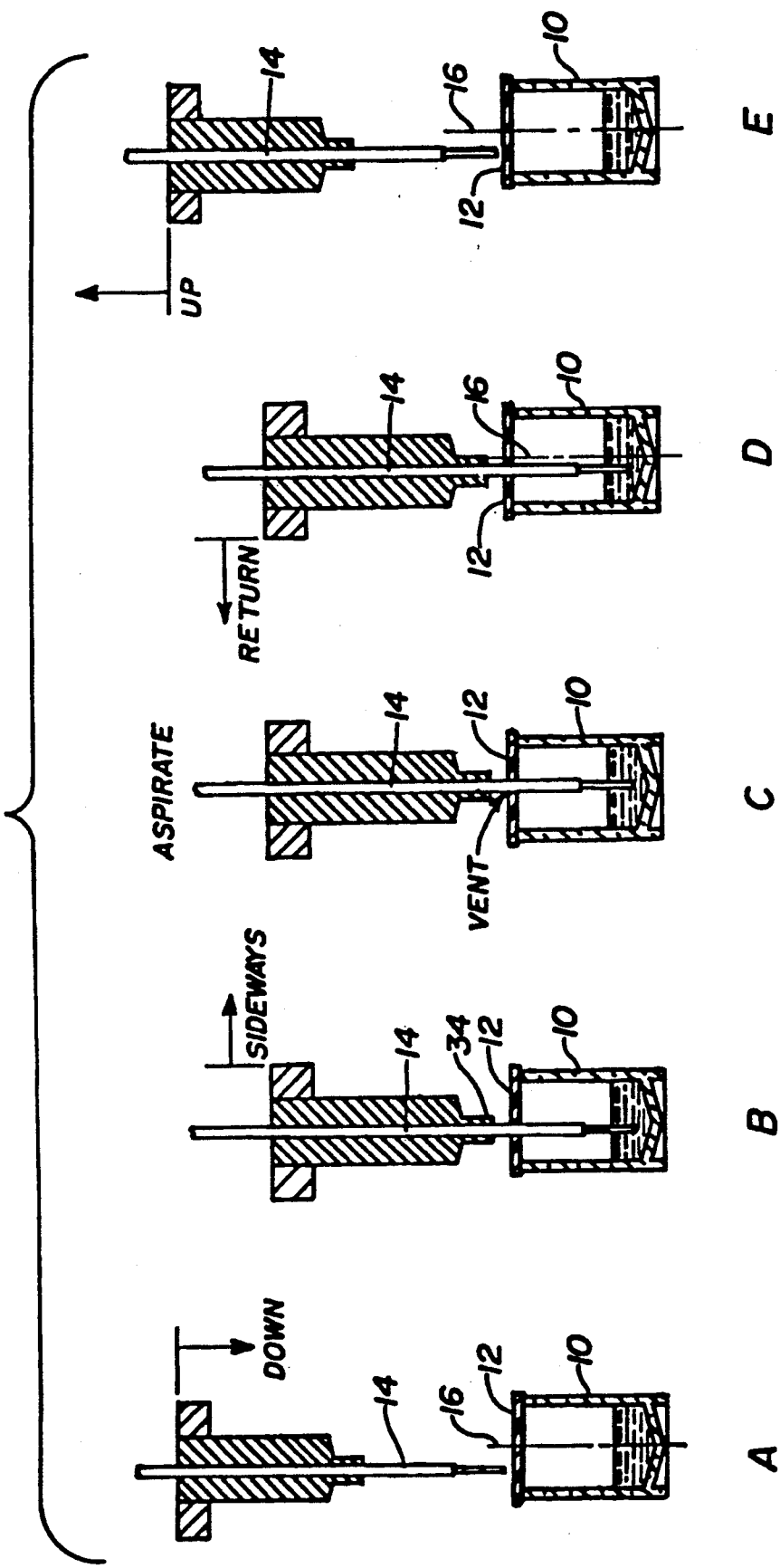
FIG. 2 is a series of diagrammatic representations of the pipette of this invention in various stages of its operation.

In the operation of this invention, which may be more easily understood with reference to FIGS. 2A through 2E, the probe 14 is initially positioned slightly off center of the axis 16 of the container 10. The amount of this offset will vary with the materials used and the diameter of the lid and the size of the probe, but typically may be in the order of 0.2 cm. Under the control of the controller 30 (FIG. 1), the probe 14 is moved downward to penetrate the lid 12 of the container 10, as is illustrated in FIG. 2B. The downward movement of the probe is stopped just before the tip 34 of the sleeve 22 touches the lid 12. Typically this clearance can be in the order of 0.015 cm to avoid contaminating the support sleeve with the reagent.

Next in accordance with this invention, the probe 14 is moved laterally as seen in FIG. 2B to lie on the axis of the container 16. This stretches the elastomeric portion of the lid 12 sufficiently to allow air to leak through the distended opening in the lid and thereby allow the pressure within the container 10 to equilibrate with that on the outside of the container, i.e., atmosphere. When the type of container used in the Dimension ® Systems is used, the lateral movement of the probe also tears the film layers which constitute a part of the elastomeric lid. Many lids were effectively vented with as little as 0.010 cm sideways motion. However, in order to ensure adequate venting, a typical sideways movement of 0.020 cm was used as a failsafe procedure. Of course with different thickness lids more or less sideways motion may be needed in order to provide an adequate "leak" about the needles to vent the container.

Of course the container must be secured against sideways motion. FIG. 1 illustrates this by 40 which may be holder for the container. The holder is attached to a rigid support 42. The holder may be a ring, clamp, or any other mechanism which prevents lateral movement of the container. While movement of the probe to the centerline of the container, i.e., the axis, is preferred, the probe movement may be chordal or radially out as desired. Movement to the axis generally accommodates the greatest probe depth.

As shown in FIG. 3C, next the pump 20 is actuated by the controller and the contents of the container 10 aspirated to achieve the sampling desired. This aspiration takes place during the period of time that the vent formed by distending the elastomeric lid 12 is open to form the "vent" as labelled in FIG. 3C. As the next, step illustrated in FIG. 4D, the probe is returned to its original position relative to the axis 16 by a return orthogonal or lateral movement. Finally as is illustrated in FIG. 2E, the probe is withdrawn from the container.

The mechanism just described facilitates a relatively simple method and provides an apparatus for venting a sealed sample container to atmosphere. It requires no additional venting needles, parts or mechanism. It requires no additional valves in the system or otherwise and yet it achieves relatively high accuracy in sampling volumes.

EXAMPLE 1

A series of experiments were run using both lidded and unlidded containers. The containers used were those sold for use with the Dimension ® System which have a lid constructed of an elastomer and film laminate.

| Performance of Various Techniques for Pipetting from a Container | | |
|---|---|---|
| | % C.V.* | Significant |
| Lidded Container | 0.58% | na, Basis for comparison |
| Unlidded Container | 0.47% | Yes, better |
| Lidded but Vented Container | 0.41% | Yes, better |
| Lidded Container using Side Stroke Method of the invention (0.20 cm) | 0.41% | Yes, better |

Where: % C.V. = (Standard Deviation/Mean)* 100

Significance is determined by doing an F-Test to determine if the difference observed is statistically significant, given the data population size.

These results show that the best performance is obtained when the container can be vented while pipetting. Either an external vent, or side stroke can be used. The side stroke method of this invention is best because it requires no secondary venting mechanisms with the attendant disadvantages. Also worth noting is that the side stroke method is best performer, even better than pipetting from a container with no lid at all. This is attributed to the wiping action provided by the lid of the container. This wiping "Squeegees" the outside of the probe, thus removing any droplets which contribute to pipetting imprecision.

We claim:

1. A method for withdrawing liquid samples from a sealed sample container having an axis, the container having an elastomeric closure, using a robotic aspirating probe, the probe affording degrees of linear motion parallel to the axis of the container and orthogonal to the axis of the container comprising the steps of:
    (a) introducing the probe through the closure into the container along an entry axis lying parallel to the axis of the container,
    (b) moving the probe orthogonally of the entry axis to stretch the closure, thereby opening a passageway adjacent the probe to atmosphere,
    (c) applying vacuum within the probe, thereby to aspirate a sample from the container, and
    (d) withdrawing the probe from the container, whereby the closing of the passageway seals the contents of the container.

2. The method of claim 1 wherein the probe is supported against bending.

3. The method of claim 1 which includes the additional step of returning the probe orthogonally to the entry axis prior to withdrawing the probe from the container.

4. The method of claim 3 wherein the probe is supported against bending.

5. The method of claim 1 wherein the entry axis and the axis of the container are the same.

6. The method of claim 5 which includes the additional step of returning the probe orthogonally to the entry axis prior to withdrawing the probe from the container.

7. The method of claim 6 wherein the probe is supported against bending.

* * * * *